United States Patent
Tixier et al.

(10) Patent No.: US 9,927,366 B2
(45) Date of Patent: Mar. 27, 2018

(54) SPECTROSCOPIC SENSOR FOR THICKNESS OR WEIGHT MEASUREMENT OF THIN PLASTIC FILMS

(71) Applicants: Sebastien Tixier, North Vancouver (CA); Frank Martin Haran, North Vancouver (CA)

(72) Inventors: Sebastien Tixier, North Vancouver (CA); Frank Martin Haran, North Vancouver (CA)

(73) Assignee: Honeywell Limited, Mississauga (CA)

( * ) Notice: Subject to any disclaimer, the term of this patent is extended or adjusted under 35 U.S.C. 154(b) by 28 days.

(21) Appl. No.: 14/667,607

(22) Filed: Mar. 24, 2015

(65) Prior Publication Data
US 2016/0282277 A1 Sep. 29, 2016

(51) Int. Cl.
*G01J 3/00* (2006.01)
*G01N 21/84* (2006.01)
(Continued)

(52) U.S. Cl.
CPC ..... *G01N 21/8422* (2013.01); *G01B 11/0625* (2013.01); *G01B 11/0675* (2013.01); *G01G 9/00* (2013.01); *G01G 9/005* (2013.01); *G01J 3/45* (2013.01); *G01N 21/31* (2013.01); *G01N 21/86* (2013.01); *G01N 21/031* (2013.01); *G01N 21/3559* (2013.01); *G01N 21/3563* (2013.01); *G01N 2021/3155* (2013.01);
(Continued)

(58) Field of Classification Search
CPC .... G01N 21/8422; G01B 11/0675; G01J 3/45
See application file for complete search history.

(56) References Cited

U.S. PATENT DOCUMENTS 3,793,524 A 2/1974 Howarth
4,311,658 A 1/1982 Nicoll
(Continued)

FOREIGN PATENT DOCUMENTS

JP 4313007 A 11/1992

OTHER PUBLICATIONS

PCT Search Report and Opinion for PCT/CA2016/000073 dated May 30, 2016.

*Primary Examiner* — Kara E Geisel
*Assistant Examiner* — Maurice Smith
(74) *Attorney, Agent, or Firm* — Charles H Jew

(57) ABSTRACT

Continuous on-line thin film measurements employ a sensor having a spectrometer for interferometric measurements and a stack of single channel detectors for adsorption measurements. The stack is separated from the spectrometer, which analyzes radiation that emerges (transmitted pass or reflected from) the film, whereas the stack analyzes radiation that has passed through the film multiple times. The spectrometer is (i) positioned directly opposite the source of radiation so that it detects transmitted radiation or (ii) disposed on the same side of the film as is the source of radiation so that the spectrometer detects radiation that is specularly reflected from the film. The sensor includes a broadband radiation source emitting visible to far infrared light which propagates through a measurement cell defined by reflective surfaces exhibiting Lambertian-type scattering. The sensor is capable of measuring thin plastic films with thicknesses down to 1 micron or less.

14 Claims, 3 Drawing Sheets

(51) Int. Cl.
    *G01B 11/06*     (2006.01)
    *G01G 9/00*     (2006.01)
    *G01J 3/45*     (2006.01)
    *G01N 21/31*     (2006.01)
    *G01N 21/86*     (2006.01)
    *G01N 21/3563*     (2014.01)
    *G01N 21/03*     (2006.01)
    *G01N 21/3559*     (2014.01)

(52) U.S. Cl.
    CPC ............... *G01N 2021/8427* (2013.01); *G01N 2021/8609* (2013.01); *G01N 2201/061* (2013.01); *G01N 2201/068* (2013.01)

(56) References Cited

U.S. PATENT DOCUMENTS

| | | |
|---|---|---|
| 4,403,010 A | 9/1983 | Festag |
| 4,582,431 A | 4/1986 | Feldman |
| 4,797,246 A | 1/1989 | Reinke |
| 4,957,770 A | 9/1990 | Howarth |
| 5,230,923 A | 7/1993 | Hirokawa |
| 5,493,401 A | 2/1996 | Horie |
| 5,543,961 A | 8/1996 | Smith |
| 5,587,792 A * | 12/1996 | Nishizawa ......... G01B 11/0625 250/559.27 |
| 5,795,394 A | 8/1998 | Belotserkovsky |
| 6,018,419 A | 1/2000 | Cobb, Jr. |
| 6,074,483 A | 6/2000 | Belotserkovsky |
| 6,179,918 B1 | 1/2001 | Belotserkovsky |
| 6,183,561 B1 | 2/2001 | Belotserkovsky |
| 6,565,343 B1 | 5/2003 | Krycki |
| 6,793,854 B1 | 9/2004 | Kirjavainen |
| 6,805,899 B2 | 10/2004 | MacHattie |
| 6,848,795 B2 | 2/2005 | Kaminsky |
| 6,999,180 B1 * | 2/2006 | Janik .................. G01B 11/2441 356/497 |
| 7,223,977 B2 | 5/2007 | Shelly |
| 7,291,856 B2 | 11/2007 | Haran |
| 7,298,492 B2 | 11/2007 | Tixier |
| 7,321,425 B2 | 1/2008 | Haran |
| 7,382,456 B2 | 6/2008 | Tixier |
| 7,436,469 B2 | 10/2008 | Gehlsen |
| 7,452,356 B2 | 11/2008 | Grove |
| 7,763,876 B2 | 7/2010 | Banton |
| 7,868,287 B2 | 1/2011 | Fry |
| 2007/0153281 A1 | 7/2007 | Gordon |
| 2010/0014164 A1 | 1/2010 | O'Brien |
| 2012/0153149 A1 | 6/2012 | Tixier |
| 2012/0305775 A1 | 12/2012 | Krolak |

* cited by examiner

SPECTROSCOPIC SENSOR FOR THICKNESS OR WEIGHT MEASUREMENT OF THIN PLASTIC FILMS

FIELD OF THE INVENTION

The present invention generally relates to sensors for measuring thin films using a combination of interferometry and near infrared absorption at fixed wavelengths.

BACKGROUND OF THE INVENTION

In the manufacture of sheet materials, it is well known that various sheet properties can be detected "on-line," that is, while a sheet making machine is operating. On-line measurement devices measure sheet properties such as thickness, basis weight, moisture content, chemical composition and the like. Typically, such on-line devices employ sensors that periodically traverse, or scan, the moving sheets in the cross direction, which is perpendicular to the machine direction of sheet travel.

Visible, near-IR and mid-IR sensors share a common need for large spectral range, high spectral resolution and high signal-to-noise ratio. A large spectral range is needed for the sensor to address a wide number of applications whereas high spectral resolution and signal-to-noise insure sensor accuracy and repeatability. However, these sensor attributes are usually mutually exclusive. For example, a single detector and filter combination affords high signal-to-noise ratio and potentially good spectral resolution but does not provide adequate spectral range. Conversely, a compact spectrometer provides high spectral range and resolution but sacrifices throughput. Additionally, while spectrometers provide high spectral range and resolution, a single unit does not cover the entire range between the visible and mid-IR due to practical and technical considerations.

Plastic and paper industrial applications require versatile detectors with the above combination of characteristics for thickness measurements. Currently, a single sensor is employed to measure the thickness of thin plastic films on biax lines. The very thin films are measured using interferometry in the visible or near-IR where absorption is weak whereas the thicker films (>15-20 microns) are measured using adsorption further out in the near-IR.

SUMMARY OF THE INVENTION

The present invention is based in part on the development of a sensor for robust, continuous on-line measurements of thin films wherein the sensor includes a spectrometer and a set or stack of single channel detectors. The stack is separated from the spectrometer, which is configured to analyze radiation that emerges (that is, transmitted through or reflected from) the film, whereas the single channel detectors are configured to analyze radiation that passed through the film multiple times. In this novel arrangement, the spectrometer is either (i) positioned directly opposite the source of radiation so that it detects radiation that passes through the film (that is, only 1 pass through the film) or (ii) disposed on the same side of the film as is the source of radiation so that the spectrometer detects radiation that is specularly reflected from the film. The single channel stack is offset from the source such that the stack detects reflected radiation that has passed multiple times through the film. The sensor is particularly suited for measuring thin plastic films especially films with thicknesses down to 1 micron or less.

Accordingly, in one aspect the invention is directed to an apparatus for sensing a layer of material that includes:

a broadband radiation source, disposed on a first side of the layer of material, that directs a beam of incident radiation into the layer of material;

a spectrometer that detects (i) transmitted radiation that passes through the layer of material or (ii) reflected radiation that is reflected from the layer of material;

a radiation receiver that detects at least a portion of a reflected beam that propagates through the layer of material; and one or more members that define a measurement cell with a path for the layer of material and wherein the measurement cell is configured to cause radiation to be reflected through the layer of material a plurality of times before being detected by the radiation receiver. In a preferred embodiment, the members (such as plates) that form the measurement cell exhibit near perfect Lambertian scattering which means that the angle at which light leaves the plate is independent of the angle at which the light impinges on the plate. This is in contrast to specular (mirror) reflection where the incident and exit angles are identical. With a Lambertian scattering surface, the angle of distribution follows a cosine law with the highest probability for the light to reflect at an angle normal to the plate but also a non-negligible probability to reflect at much smaller angles (for example, 45 degrees) therefore allowing the light to travel across the entire area of the plates. The Lambertian-type light scattering that is generated allows the light to interact multiple times with the layer(s) of material, thus, the radiation receiver's sensitivity to selected components within the layer is enhanced.

In another aspect, the invention is directed to a method for measuring a plurality of characteristics of a flat sheet product which includes:

(a) emitting broadband radiation that ranges from visible to far infrared radiation towards the flat sheet product;

(b) analyzing reflected radiation that has propagated through the flat sheet product a plurality of times to measure characteristics using adsorption techniques; and (c) analyzing (i) transmitted radiation that passes through the flat sheet product or (ii) reflected radiation that is reflected from the flat sheet product to measure characteristics using a spectrometer when interference is detected.

The spectrometer measures the optical thickness of the sheet using conventional thin film interferometry when interferences are detected. The visibility (amplitude) of the thickness fringes have to be large enough so the measurement is robust. Visibility of the interference pattern is defined as (Max−Min)/(Max+Min) where Max and Min are the maximum and minimum values of the interference spectrum. When or if the fringe visibility is too low, the sensor measures the product thickness using the multi-wavelength absorption technique.

Both interferometry and adsorption measurements can be performed simultaneously to generate a thickness profile that consist of one or both measurements. In this fashion, physical characteristics such as film thickness can be ascertained continuously even if the film thickness fluctuates. The thickness measurement obtained from interferometry by employing the spectrometer is typically superior to the measurement obtained by absorption when the visibility is greater than a certain limit. The appropriate limit can be found experimentally. It can be in the range of 0.1 to 5%. It can also be a dynamic limit based on the signal-to-noise ratio of the measurement or of the 2-sigma accuracy of the fit to the interference pattern.

Typically, the spectrometer analyzes radiation in a first radiation range and the radiation receiver analyzes radiation in a second radiation range with the spectrometer analyzing visible, a near infrared, mid-infrared spectral range, or far infrared spectral range. The spectrum characteristic of the spectrometer and the spectrum characteristic of one of said plurality of channel detectors can be designed to overlap or not overlap.

The absorption measurement can also be used to decide which of absorption or interferometry is better to use. In this case, the calculated thickness by absorption should be greater than a certain value (typically around 10-12 microns) for absorption to be used and optical thickness by interferometry to be ignored.

DETAILED DESCRIPTION OF PREFERRED EMBODIMENTS

Figure 1:
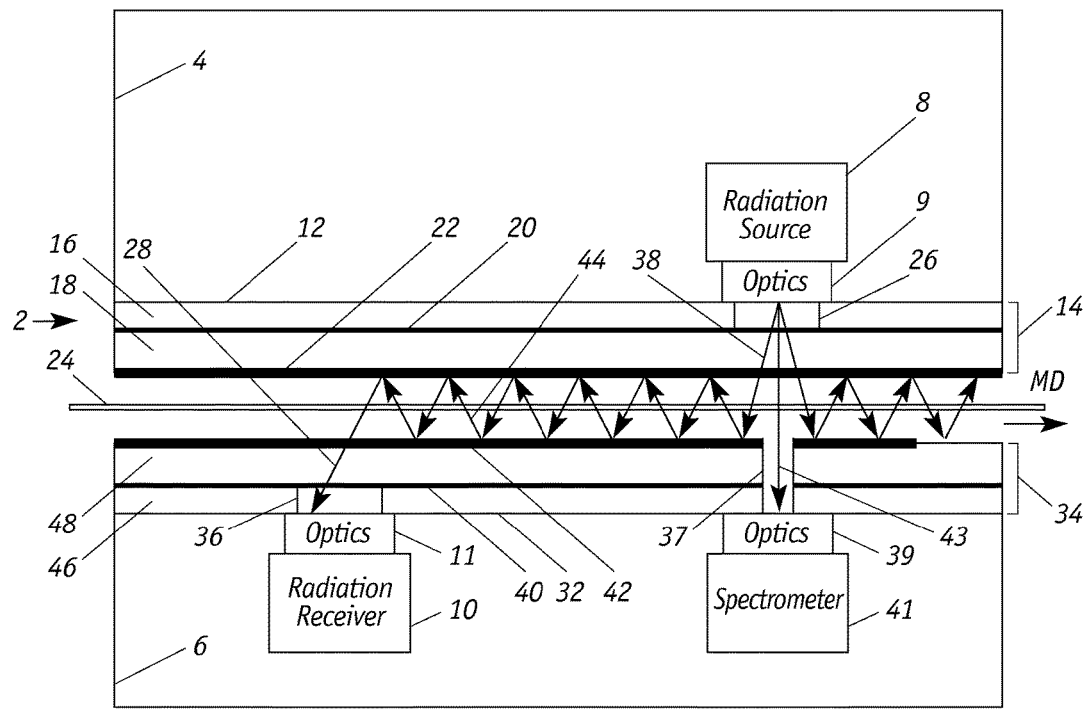
FIGS. 1, 2, 3, and 4 depict spectrometer/adsorption thickness sensors of the present invention.

FIG. 1 illustrates a non-contacting optical sensor 2 that includes enclosures 4 and 6 (each also called "scanner head" or "head") that house sensor components for measuring qualities, characteristics or features of a moving web 24 that can be monitored which include, but are not limited, to single and multi-layered compositions, coatings, films, webs or sheets. While the sensor will be illustrated in measuring characteristics in paper and plastic, it is understood that the sensor can be employed to detect a variety of components in a number of different materials including, for example, coated materials, fabrics, and the like. Sensor 2 is particularly suited for measuring the thickness or weight of a layer of light transmissive material 24 moving in the machine direction (MD). Scanner 2 includes a radiation or light source 8 that is positioned in head 4 and spectrometer 41 and a radiation receiver or detector 10 that are both positioned in head 6. An upper diffuse reflector plate assembly 14, which is secured to operative surface 12 of head 4, comprises a reflective element 16, such as a specular mirror, that is covered with a layer or plate 18 of calcium fluoride (CaF$_2$), sapphire or quartz glass. A specular mirror can comprises an aluminum coating formed on a polyimide which is available as KAPTON film. Outer surface 22 of layer 18 is preferably polished to make it easier to clean and to render it more resistant to moisture whereas inner surface 20 is highly roughened to serve as a diffusive surface. Similarly, a lower diffuse reflector plate assembly 34, which is secured to operative surface 32 of head 6, comprises a reflective element 46, such as a specular mirror, that is covered with a layer or plate 48 of calcium fluoride, sapphire or quartz glass. Outer surface 42 of layer 48 can also be polished whereas inner surface 40 is highly roughened to serve as a diffusive surface. These reflective and diffusive plates work well in the 300 nm to 5 micron radiation range. In a preferred embodiment, each of the upper and lower diffuse reflector plates assemblies 14, 34 comprises a specular reflective surface with a diffusive layers consisting of microporous polytetrafluoroethylene (PTFE) covered with quartz glass.

The upper and lower scanner heads 4, 6 are aligned so that planar polished surface 22 of upper scanner head 4 is parallel with and faces planar polished surface 42 of the lower scanner head 6. Apertures 26, 37 and 36 provide access to light source 8, spectrometer 41 and receiver 10, respectively. Apertures 26 and 37, which are configured on opposite sides of moving web 24, are aligned so that spectrometer 41 detects radiation that is transmitted through web 24. Apertures 26 and 36, which are also configured on opposite sides of moving web 24, are not aligned, that is, as shown, light source 8 and receiver 10 define respective axes of radiation that are laterally offset from one another along the MD path of moving web 24. In this fashion, the arrangement of upper and lower diffuse reflector plates 14, 34 define a measurement window or cell through which web material 24 travels.

In operation of sensor 2, optics 9 such as a focusing lens in light source 8 focuses incident radiation 38 through aperture 26 toward moving web 24. Optics 39 such as a collimating or conditioning lens is positioned to collection radiation 43 that is transmitted through web 24 and optics 11 such as a collimating or conditioning lens is positioned to collect radiation 28, which is diffusively reflected from diffuse reflector plate 14, through aperture 36. Movement of the upper and lower scanner heads 4, 6 in the cross direction, which is traverse to the MD, is coordinated so that light is diffused and reflected by plate assemblies 14, 34 as radiation 44 propagates through layer of material 24 multiple times before being detected by receiver 10.

Light diffusing elements that scatter or diffuse light generally function in one of three ways: (a) as a surface light diffusing element utilizing surface roughness to scatter light in a number of directions, (b) as a bulk light diffusing element with flat outer surfaces and embedded light-scattering elements, or (c) as a combination of elements (a) and (b). The bulk diffuser diffuses the light within the material. Diffusion is achieved by light scattering as it passes through materials with varying indexes of refraction. The term "diffuser" or "diffuser member" means any material that is able to diffuse specular light (light with a primary direction) to a diffuse light (light with random direction). The term "light" means electromagnetic radiation having wavelength in ranges that are suited for measuring properties of a layer material with sensors of the present invention. Near infrared and/or mid-infrared radiation is particularly suited for measuring physical characteristics of paper and plastic products.

Calcium fluoride, sapphire, and quartz glass are transparent to near and mid-infrared radiation. The randomly roughened surfaces 20, 40 can be produced by electric discharge techniques, mechanical grinding, or etching to create a plurality of randomly oriented and spaced facets and cavities for diffusively reflecting incident near and mid infrared radiation.

Light source 8 can comprise, for instance, a Quartz Tungsten Halogen lamp to irradiate material 24 with radiation having wavelengths in at least first and second separate wavelength regions of the electromagnetic spectrum that are referred to as reference and measurement wavelength bands as further described herein.

Spectrometer 41 can comprise, for instance, a grating based or linear variable filter (LVF) based array spectrometer. Acousto-Optic Tunable Filter (AOTF) spectrometer, Fourier Transform InfraRed (FTIR) spectrometer and Fabry-Perot spectrometer can also be employed.

In the arrangement of radiation source 8, radiation receiver 10 shown in FIG. 1, reflected light 44 travels in a direction that is parallel to the MD so that the cross direction (CD) resolution of sensor 2 is maintained. Although reflected radiation 44 shown in FIG. 1 is depicted as traveling "downstream" in the opposite machine direction as web 24, this feature is not critical to the sensor's function.

In other words, sensor 2 will operate even if web 24 moves in the opposite direction so that the reflected radiation is moving "upstream" relative to the web; the critical feature is that incident radiation 38 that emitted from light source 8 travel along a path that is parallel to that of moving web 24 as reflected radiation 44 moves toward receiver 10.

Figure 2:
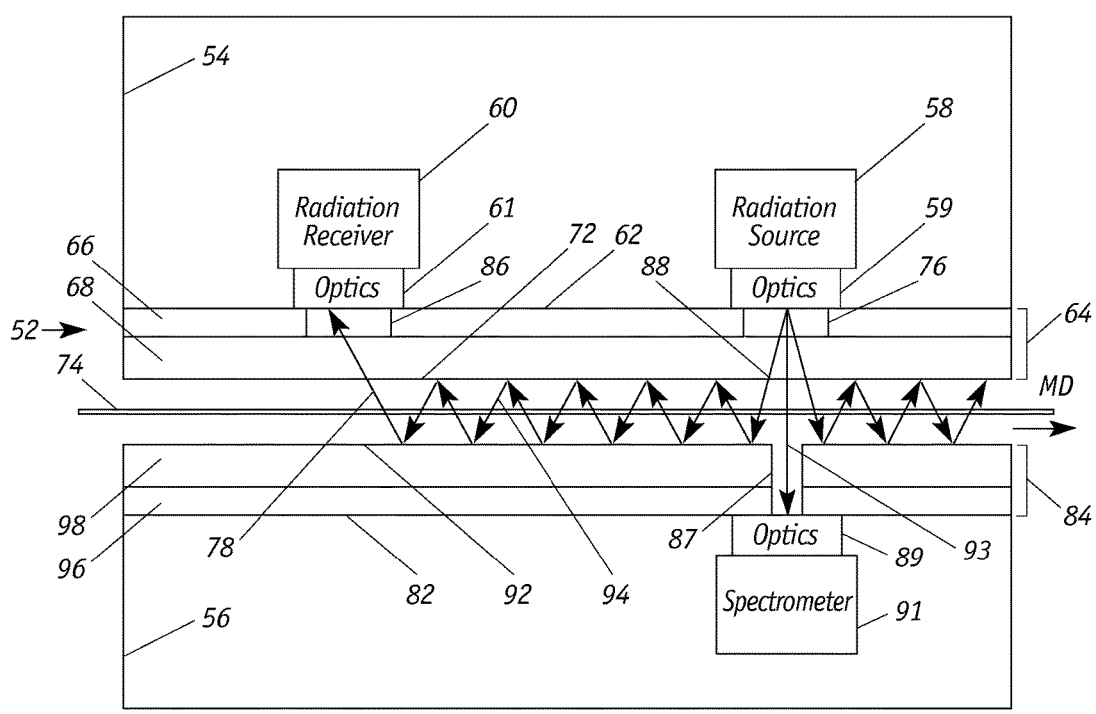

FIG. 2 illustrates a non-contacting optical sensor 52, which includes scanner head 54 that houses light source 58 and receiver or detector 60 and scanner head 56 that houses spectrometer 91. Sensor 52 measures physical qualities, characteristics or features of a layer of light transmissive material 74 moving in the MD. An upper diffuse reflector plate assembly 64, which is secured to operative surface 62 of head 54, comprises a reflective element 66, such as a specular mirror, that is covered with a layer or plate 68 made of alumina ($Al_2O_3$). Similarly, a lower diffuse reflector plate assembly 84, which is secured to operative surface 82 of head 56, comprises a reflective element 96, such as a specular mirror, that is covered with a layer or plate 98 of alumina.

The upper and lower scanner heads 54, 56 are aligned so that planar surface 72 of alumna plate 68 is parallel with and faces planar surface 92 of alumina plate 98. Apertures 76, 87 and 86 provide access to light source 58, spectrometer 91 and receiver 60, respectively, and they can be equipped with a window material, which can be roughened on one side or not, such as calcium fluoride, sapphire or quartz glass. The upper and lower diffuse reflector plates 64, 84 form a measurement window or cell through which web material 74 travels. In operation of sensor 52, optics 59 in light source 58 focuses incident radiation 88 through aperture 76 toward moving web 74. Optics 89 captures radiation 93 into spectrometer 91 and optics 61 collects radiation 78 that is reflected from surface 92 through aperture 86. Movement of the upper and lower scanner heads 54, 56 in the cross direction is coordinated so that light is diffused and reflected between plate assemblies 64, 84 as radiation 94 propagates through layer of material 74 multiple times before being detected by receiver 60. Alumina, which is translucent to near and mid infrared radiation, serves as a bulk light-diffusing element. The alumina layer is typically smooth on both sides.

Figure 3:
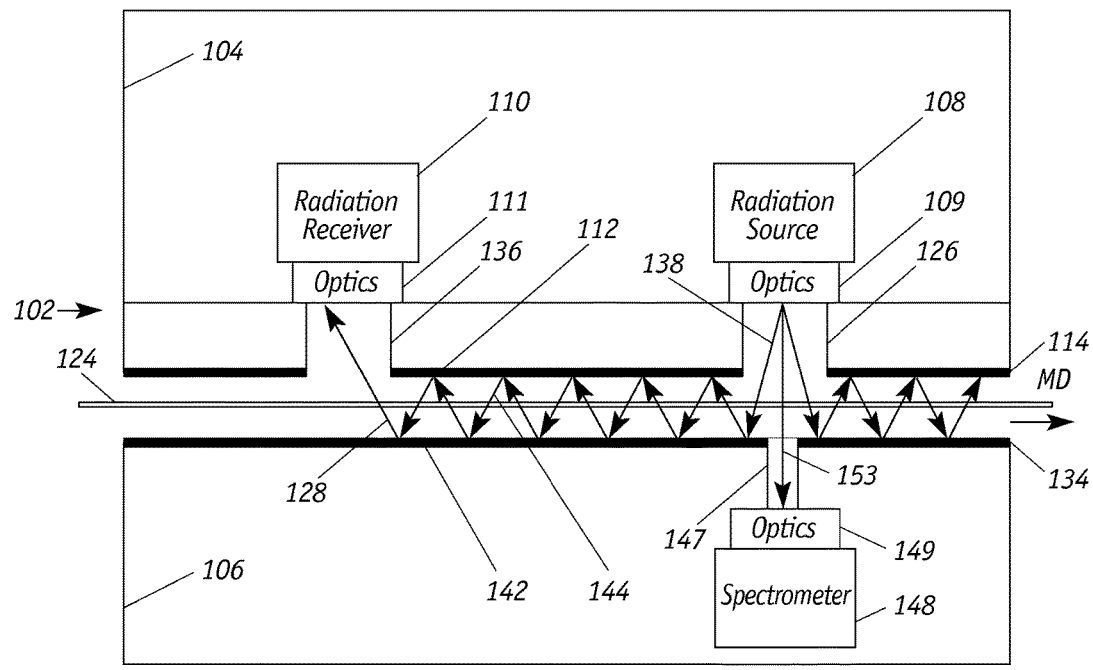

FIG. 3 illustrates another non-contacting optical sensor 102, which includes scanner head 104 that houses light source 108 and receiver or detector 110 and scanner head 106 that houses spectrometer 148. Sensor 102 measures physical qualities, characteristics, or features of a layer of light transmissive material 124 moving in the MD. An upper diffuse reflector plate assembly 114, which is formed on operative surface 112 of head 104, comprises a reflective element consisting of a roughened operative surface that is coated with a metallic reflective coating. Alternatively, the reflective element consists of a diffusively reflective metallic surface. Similarly, a lower diffuse reflector plate assembly 134 has an operative surface 142 on head 106 that has a reflective element of the same construction. Suitable metallic coatings can be formed, for example, from gold, silver, and aluminum by electrochemical plating.

The upper and lower scanner heads 104, 106 are aligned so that surface 112 of upper scanner head 104 is parallel with and faces surface 142 of lower scanner head 106. Apertures 126, 147 and 136 provide access to light source 108, spectrometer 148 and receiver 110, respectively; the apertures can be optionally equipped with a calcium fluoride, sapphire or quartz glass window, which is roughened on one side or not. The upper and lower diffuse reflector plates 114, 134 define a measurement window or cell through which web material 124 travels. In operation of sensor 102, optics 109 in light source 108 focuses incident radiation 138 through aperture 126 toward moving web 124. Optics 149 collects radiation 153 into spectrometer 148 and optics 111 collects radiation 128 that is reflected from surface 142 through aperture 136. Movement of the upper and lower scanner heads 104, 106 in the cross direction is coordinated so that light is diffused and reflected between plate assemblies 114 and 134 as radiation 144 propagates through layer of material 124 multiple times before being detected by receiver 110. In this sensor 102, the roughened metallic coating (or the diffusively reflective metallic surface) functions both as diffuser and reflective elements.

Figure 4:
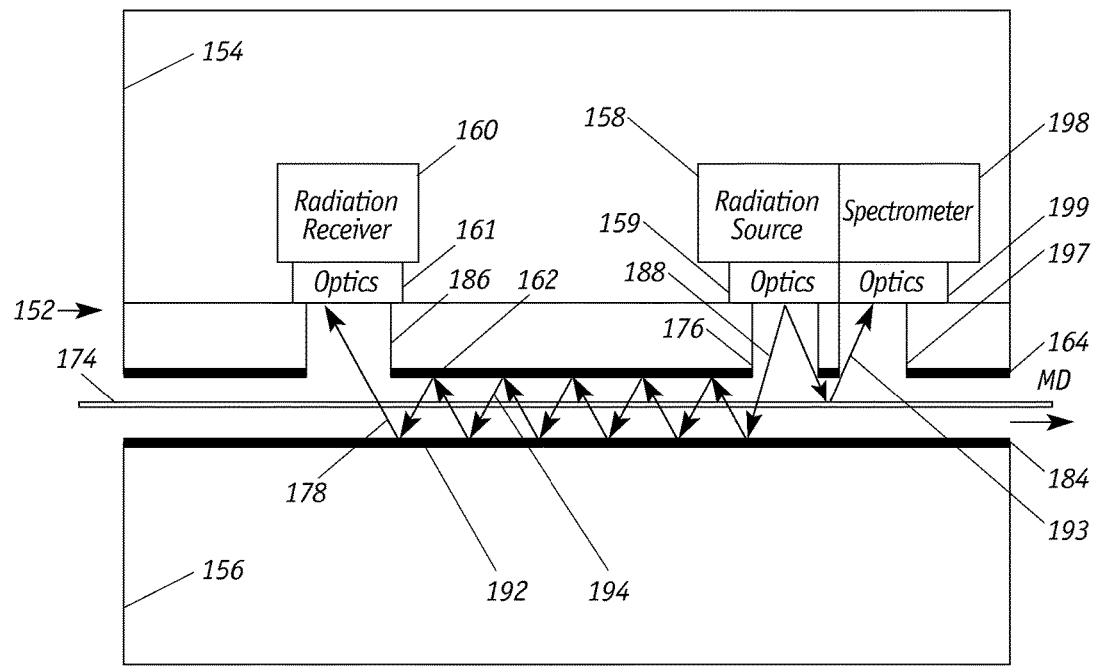

FIG. 4 illustrates an embodiment of a non-contacting optical sensor where the spectrometer and the source of radiation are located on the same side of the moving web 174. In this fashion, the spectrometer detects radiation that is reflected specularly from moving web or sheet 174. Optical sensor 152 scanner head 154 houses light source 158, receiver or detector 160, and spectrometer 198 with spectrometer 198 being positioned upstream of radiation source 158. Sensor 152 measures physical qualities, characteristics, or features of a layer of light transmissive material 174 moving in the MD. An upper diffuse reflector plate assembly 164, which is formed on operative surface 162 of head 154, comprises a reflective element consisting of a roughened operative surface that is coated with a metallic reflective coating. Alternatively, the reflective element consists of a diffusively reflective metallic surface. Similarly, a lower diffuse reflector plate assembly 184 has an operative surface 192 on head 156 that has a reflective element of the same construction. Suitable metallic coatings can be formed, for example, from gold, silver, and aluminum by electrochemical plating.

The upper and lower scanner heads 154, 156 are aligned so that surface 162 of upper scanner head 154 is parallel with and faces surface 192 of lower scanner head 156. Apertures 176, 197 and 186 provide access to light source 158, spectrometer 198 and receiver 160, respectively; the apertures can be optionally equipped with a calcium fluoride, sapphire or quartz glass window, which is roughened on one side or not. The upper and lower diffuse reflector plates 164, 184 define a measurement window or cell through which web material 174 travels. In operation of sensor 152, optics 159 in light source 158 focuses incident radiation 188 through aperture 176 toward moving web 174. Optics 199 collects radiation 193 into spectrometer 198 and optics 161 collects radiation 178 that is reflected from surface 192 through aperture 186. Movement of the upper and lower scanner heads 154, 156 in the cross direction is coordinated so that light is diffused and reflected between plate assemblies 164 and 184 as radiation 194 propagates through layer of material 174 multiple times before being detected by receiver 160. In this sensor 152, the roughened metallic coating (or the diffusively reflective metallic surface) functions both as diffuser and reflective elements.

Figure 5:
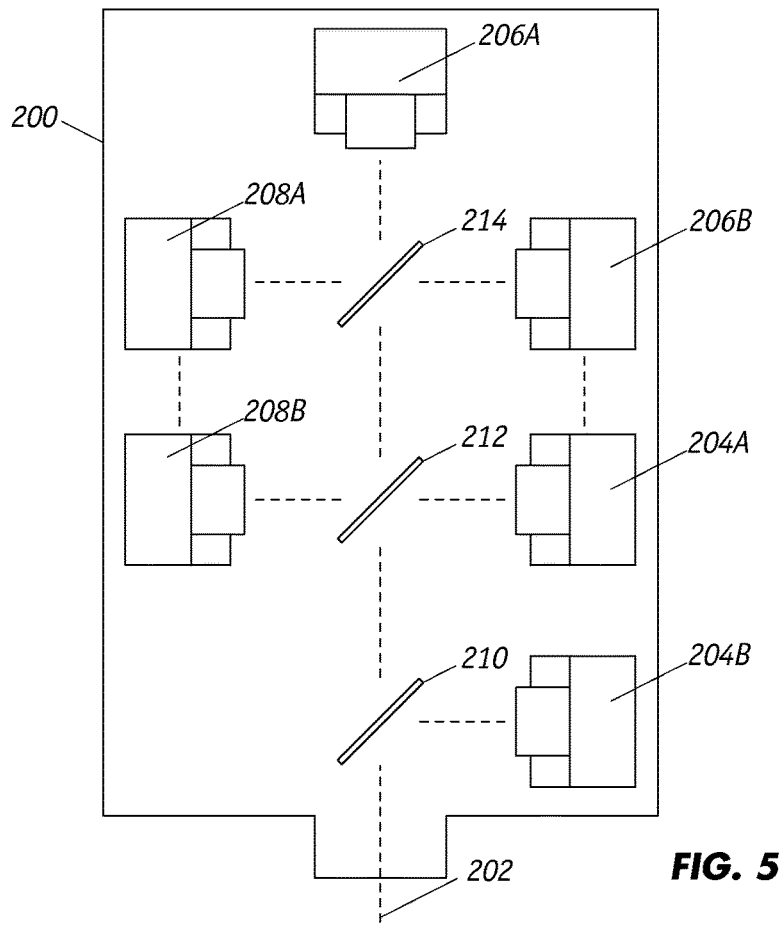
FIG. 5 illustrates a light receiver.

FIG. 5 illustrates a suitable receiver that includes a detector assembly 200 that houses a six-channel sensor for measuring three properties in a layer of material. In this arrangement, there are three measurement filter/detectors 204A, 206A and 208A and three corresponding reference filter/detectors 204B, 206B, and 208B. A separate infrared band pass filter is positioned before each detector; in this fashion, each of the infrared detectors measures the intensity of only the portion of the infrared beam spectrum that falls within the band pass of the associated filter. A broadband infrared source of energy (not shown) directs incident radiation onto the layer of material to be analyzed and reflected radiation 202 is wavelength-analyzed by passing the beam through beam splitters 210, 212, 214 and the appropriate filters to the individual detectors. As is apparent, additional pairs of measure and reference detector/filters can be incorporated as needed.

Figure 6:
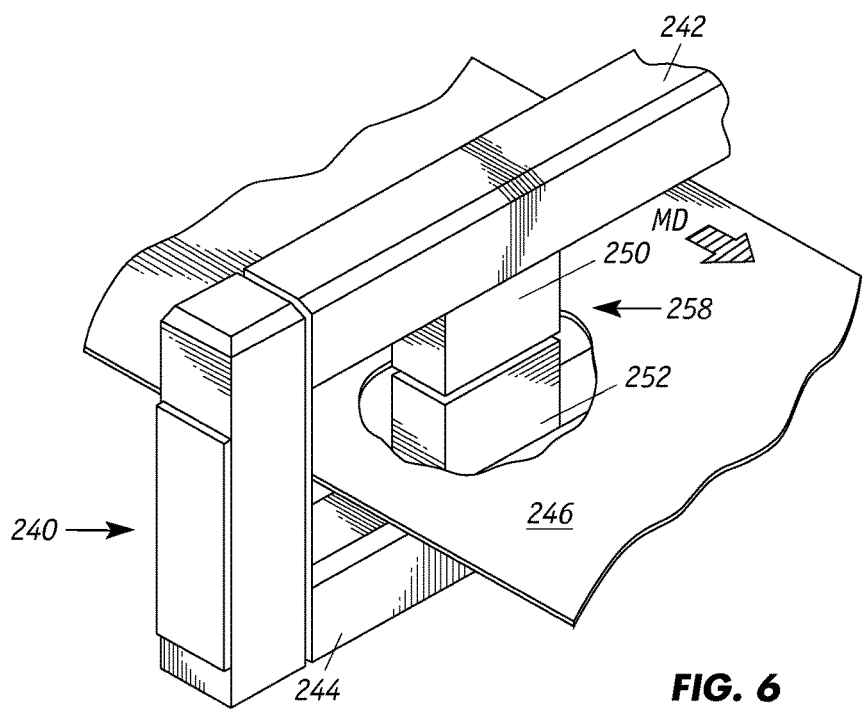
FIG. 6 shows a sheetmaking system implementing the sensor in a dual head scanner.

FIG. 6 illustrates one particular implementation of the sensors that are shown in FIGS. 1, 2, 3, and 4. In particular, the radiation source and detector are housed in a dual head scanner 258 of scanner system 240 which can be employed to measure the moisture content in paper or the concentration of polymer films. Upper scanner head 250 moves repeatedly back and forth in the CD across the width of the moving sheet 246, which moves in the MD, so that the characteristics of the entire sheet may be measured. Scanner 258 is supported by two transverse beams 242, 244 on which are mounted upper and lower scanning heads 250, 252. The operative faces of the lower and upper scanner heads 250, 252 define a measurement window or cell that accommodates sheet 246. The lower scanner head 252 may include a sheet stabilization system such as an air-bearing stabilizer (not shown) to maintain the sheet on a consistent plane as it passes through the measurement cell. The movement of the dual scanner heads 250, 252, is synchronized with respect to speed and direction so that they are aligned with each other.

One technique of monitoring the thickness of a plastic film measures the concentration(s) (weights per unit area, typically measured in grams per square meter, gsm) of the particular polymer(s) that form the film. Multilayer films typically comprise a plurality of layers that are laminated together. Preferably, in the multilayer structure, adjacent layers are formed of different polymer materials. By employing different polymers with different physical properties, the multilayer film may have a combination of physical attributes not present in a single layer film. For example, the multilayer film may be moisture resistant, abrasion resistant, and yet remain pliable. The sensor of the present invention, among other things, is effective in controlling the production of multilayer films to assure that each layer in the film has the proper thickness or weight (gsm) so that the multilayer film has the right combination of properties.

If the density of a particular polymer component in the multilayer film is known the thickness of the film component can be determined. The thickness can be calculated with a computer. The film thickness may not always be calculated and the weight (gsm) of the component is all that is required by the user for quality control. In the production of monopolymers, film thickness is typically calculated.

The foregoing has described the principles, preferred embodiments and modes of operation of the present invention. However, the invention should not be construed as being limited to the particular embodiments discussed. Thus, the above-described embodiments should be considered as illustrative rather than restrictive, and it should be appreciated that variations may be made in those embodiments by workers skilled in the art without departing from the scope of the present invention as defined by the following claims.

What is claimed is:

1. An apparatus for sensing a layer of plastic material that comprises:
   a radiation source, disposed on a first side of the layer of plastic material, that directs a beam of incident radiation into the layer of plastic material wherein the radiation source emits broadband radiation from the visible to the far infrared region;
   a spectrometer, configured to detect interference, that detects transmitted broadband radiation that passes through the layer of plastic material;
   a radiation receiver that detects at least a portion of a reflected beam of broadband that propagates through the layer of material wherein the radiation receiver comprises at least one of a plurality of single channel detectors, wherein the spectrometer analyzes broadband radiation in a first radiation range and the radiation receiver analyzes broadband radiation in a second radiation range wherein a spectrum characteristic of the spectrometer and a spectrum characteristic of all of said plurality of channel detectors do not overlap and wherein the spectrometer and the radiation receiver operate simultaneously: and
   one or more members with reflective surfaces that define a measurement cell with a path for the layer of plastic material and wherein the measurement cell is configured to cause broadband radiation to be reflected through the layer of material a plurality of times before being detected by the radiation receiver wherein the reflected broadband radiation propagating through the measurement cell exhibit Lambertian-type scattering.

2. The apparatus of claim 1 wherein the spectrometer, which is disposed on a second side of the layer of plastic material and opposite the radiation source.

3. The apparatus of claim 1 wherein the pair of members includes a first member that has a first plate and a second member that includes a second plate, wherein the first and second plates are substantially parallel and the plates are positioned on opposite sides and substantially parallel to the layer of plastic material, wherein the first plate has a first aperture that is coupled to the radiation source and wherein the second plate has a second aperture that is coupled to the radiation receiver.

4. The apparatus of claim 1 wherein the pair of members includes a first member that has a first plate and a second member that includes a second plate, wherein the first plate and second plate are substantially parallel and the plates are positioned on the opposite sides and substantially parallel to the layer of plastic material, wherein the first plate has a first aperture that is coupled to the radiation source and wherein the first plate has a second aperture that is coupled to the radiation receiver.

5. The apparatus of claim 1 wherein the spectrometer is one of in a visible spectral range, in a near infrared spectral range, in a mid-infrared spectral range, and in a far infrared spectral range.

6. The apparatus of claim 1 comprising a pair of members that defines a measurement cell for the layer of plastic material, wherein the radiation source and radiation receiver have respective axes of radiation and detection that are laterally offset from one another with respect to the path.

7. The apparatus of claim 1 the radiation receiver comprising:
   a plurality of beam splitters for splitting the reflected beam radiation;
   a plurality of bandpass filters for filtering the reflected beam radiation; and
   a plurality of single channel detectors, each channel detector being coupled to one bandpass filter with each coupled channel detector and bandpass filter measures one or more characteristics of said plurality of characteristics of the layer of plastic material using said split radiation received from one or more of said plurality beam splitters, said characteristics measured by each coupled channel detector and bandpass filter being different from the characteristics measured by the spectrometer.

8. The apparatus of claim 1 wherein each member includes a diffuser, facing a side of the layer of material, that comprises of (i) at least one layer of material that comprises calcium fluoride, sapphire, quartz glass and/or alumina that is formed on a specular reflective surface or (ii) a diffusively reflective surface comprising metallic layer with a rough surface, wherein the measurement cell is configured to cause broadband radiation to be reflected through the layer of plastic material a plurality of times before being detected by the radiation receiver.

9. The apparatus of claim 1 wherein each member includes a diffuser, facing a side of the layer of plastic material, that comprises a reflective surface securing a layer of PTFE, which is covered by quartz glass.

10. A method for measuring a plurality of characteristics of a flat sheet of plastic which comprises:
    (a) emitting broadband radiation towards the flat sheet of plastic;
    (b) analyzing reflected broadband radiation, with a radiation receiver which comprises at least one of a plurality of single channel detectors, that has propagated through the flat sheet of plastic a plurality of times to measure characteristics using adsorption techniques by propagating the reflected broadband radiation through a measurement cell defined by reflective surfaces exhibiting Lambertian-type scattering; and
    (c) analyzing transmitted broadband radiation that passes through the flat sheet of plastic with a spectrometer when interference is detected wherein the spectrometer analyzes broadband radiation in a first radiation range and the radiation receiver analyzes broadband radiation in a second radiation range wherein a spectrum characteristic of the spectrometer and a spectrum characteristic of all of said plurality of channel detectors do not overlap and wherein steps (b) and (c) are performed simultaneously to generate a thickness profile.

11. The method of claim 10 wherein step (a) emits broadband radiation that ranges from visible to far infrared.

12. The method of claim 10 wherein flat sheet of plastic comprises polymeric film.

13. An apparatus for sensing a layer of plastic material that comprises:
    a radiation source, disposed on a first side of the layer of plastic material, that directs a beam of incident radiation into the layer of plastic material wherein the radiation source emits broadband radiation from the visible to the far infrared region;
    a spectrometer, configured to detect interference, which is disposed on the second side of the layer of plastic material and opposite the radiation source, and that detects transmitted broadband radiation in the visible or near-infrared spectra range that passes through the layer of plastic material wherein the spectrometer analyzes broadband radiation in a first radiation range;
    a radiation receiver that detects at least a portion of a reflected beam of broadband radiation that propagates through the layer of plastic material where the radiation receiver analyzes broadband radiation in a second radiation range, wherein the radiation receiver comprises at least one of a plurality of single channel detectors and wherein a spectrum characteristic of the spectrometer and a spectrum characteristic of all of said plurality of single channel detectors do not overlap; and
    one or more members with reflective surfaces that define a measurement cell with a path for the layer of plastic material and wherein the measurement cell is configured to cause broadband radiation to be reflected through the layer of plastic material a plurality of times before being detected by the radiation receiver wherein the reflected radiation propagating through the measurement cell exhibit Lambertian-type scattering.

14. The apparatus of claim 13 wherein the spectrometer and the radiation receiver operate simultaneously.

* * * * *